(12) United States Patent
Awasthi et al.

(10) Patent No.: US 7,994,356 B2
(45) Date of Patent: Aug. 9, 2011

(54) MONO ETHYLENICALLY UNSATURATED POLYCARBOSILOXANE MONOMERS

(75) Inventors: Alok Kumar Awasthi, Pittsford, NY (US); Jason K. Stanbro, Rochester, NY (US); Jay F. Kunzler, Canandaigua, NY (US); Jeffrey G. Linhardt, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 59 days.

(21) Appl. No.: 12/499,854

(22) Filed: Jul. 9, 2009

(65) Prior Publication Data
US 2011/0009658 A1    Jan. 13, 2011

(51) Int. Cl.
*C07F 7/02* (2006.01)
*C07F 7/10* (2006.01)

(52) U.S. Cl. ......... 556/419; 556/418; 556/434; 556/439
(58) Field of Classification Search ................... 556/418, 556/419, 434, 439
See application file for complete search history.

(56) References Cited

U.S. PATENT DOCUMENTS

| | | | |
|---|---|---|---|
| 3,808,179 A | 4/1974 | Gaylord | |
| 4,208,506 A | 6/1980 | Deichert et al. | |
| 4,433,125 A * | 2/1984 | Ichinohe et al. | 526/279 |
| 4,525,563 A * | 6/1985 | Shibata et al. | 526/279 |
| 4,665,145 A * | 5/1987 | Yokota et al. | 526/279 |
| 4,686,267 A | 8/1987 | Ellis et al. | |
| 5,034,461 A | 7/1991 | Lai et al. | |
| 5,070,215 A | 12/1991 | Bambury et al. | |
| 5,321,108 A | 6/1994 | Kunzler et al. | |
| 5,358,995 A | 10/1994 | Lai et al. | |
| 5,374,662 A | 12/1994 | Lai et al. | |
| 5,387,632 A | 2/1995 | Lai et al. | |
| 5,387,662 A | 2/1995 | Kunzler et al. | |
| 5,420,324 A | 5/1995 | Lai et al. | |
| 5,451,651 A | 9/1995 | Lai | |
| 5,496,871 A | 3/1996 | Lai et al. | |
| 5,539,016 A | 7/1996 | Kunzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 5,831,110 A | 11/1998 | Isoda et al. | |
| 5,998,498 A | 12/1999 | Vanderlaan et al. | |
| 6,306,992 B1 * | 10/2001 | Yoshitake et al. | 526/279 |
| 6,367,929 B1 | 4/2002 | Maiden et al. | |
| 6,921,802 B2 | 7/2005 | Kunzler et al. | |
| 6,943,203 B2 | 9/2005 | Vanderlaan et al. | |
| 2009/0168013 A1 | 7/2009 | Kunzler et al. | |

FOREIGN PATENT DOCUMENTS

| | | |
|---|---|---|
| WO | WO 97/20851 | 6/1997 |
| WO | WO 2008/092048 | 7/2008 |
| WO | WO 2009/009527 | 1/2009 |

OTHER PUBLICATIONS

Lai, Yu-Chin. "The Role of Bulky Polysiloxanylalkyl Methacrylates in Oxygen-Permeable Hydrogel Materials" in J. Appl. Poly. Sci., vol. 56, pp. 317-324 (1995).
Lai, Yu-Chin. "The Role of Bulky Polysiloxanylakyl Methacrylates in Polyurethane-Polysiloxane Hydrogels" in J. App. Poly. Sci., vol. 60, pp. 1193-1199 (1996).
Benjamin, William J. et al. "The Oxygen Permeability of Reference Materials" in Optom. Vis. Sci., 74 (12s): 95 (1997).
Lohmeijer, Bas G.G. et al. "Organocatalytic Living Ring-Opening Polymerization of Cyclic Carbosiloxanes" in Organic Letters, vol. 8, No. 21, pp. 4683-4686 (2006).
Lu, Ping et al."Reaction of Dimethyldichlorosilane, Phenylmethyldichlorosilane, or Diphenyldichlorosilane with Dimethyl Sulfoxide" in Organometallics, 1996, 15, pp. 4649-4652.
Piccoli, William et al. "Highly Strained Cyclic-Paraffin Siloxanes" in Organic and Biological Chemistry, Apr. 20, 1960, vol. 82, pp. 1883-1885.
Ziatdinov, Vadim et al. Anionic Ring-Opening Polymerization of Trimethylsiloxy-Substituted 1-Oxa-2,5-disilacyclopentanes..: in Macromolecules, 2002, vol. 35, pp. 2892-2897.
U.S. Appl. No. 12/499,853, filed Jul. 9, 2009, Awasthi et al.
International Search Report (PCT/ISA/210) and Written Opinion (PCT/ISA/237) mailed on Mar. 30, 2011.

* cited by examiner

*Primary Examiner* — Porfirio Nazario Gonzalez
(74) *Attorney, Agent, or Firm* — Glenn D. Smith

(57) ABSTRACT

The present invention relates to polymeric compositions useful in the manufacture of biocompatible medical devices. More particularly, the present invention relates to certain monoethylenically unsaturated polycarbosiloxane monomers capable of polymerization to form polymeric compositions having desirable physical characteristics useful in the manufacture of ophthalmic devices.

6 Claims, No Drawings

MONO ETHYLENICALLY UNSATURATED POLYCARBOSILOXANE MONOMERS

PRIORITY CLAIMS TO PRIOR APPLICATIONS

None

CROSS-REFERENCE TO RELATED APPLICATIONS

None

FIELD

The present invention relates to novel monomers useful in the manufacture of biocompatible medical devices. More particularly, the present invention relates to certain monomers based on mono ethylenically unsaturated polycarbosiloxane monomers capable of polymerization to form polymeric compositions having desirable physical characteristics useful in the manufacture of ophthalmic devices. Such properties include low modulus of elasticity and improved hydrolytic stability.

BACKGROUND AND SUMMARY

Various articles, including biomedical devices, are formed of organosilicon-containing materials. One class of organosilicon-containing materials useful for biomedical devices, such as soft contact lenses, is silicone-containing hydrogel materials. A hydrogel is a hydrated, crosslinked polymeric system that contains water in an equilibrium state. Hydrogel contact lenses offer relatively high oxygen permeability as well as desirable biocompatibility and comfort. The inclusion of a silicone-containing material in the hydrogel formulation generally provides higher oxygen permeability since silicone based materials have higher oxygen permeability than water.

Organosilicon-containing materials useful for biomedical devices, including contact lenses, are disclosed in the following U.S. patents: U.S. Pat. No. 4,208,506 (Deichert et al.); U.S. Pat. No. 4,686,267 (Ellis et al.); U.S. Pat. No. 5,034,461 (Lai et al.); and U.S. Pat. No. 5,070,215 (Bambury et al.).

U.S. Pat. Nos. 5,358,995 and 5,387,632 describe hydrogels made from various combinations of silicone macromers, TRIS, n-vinyl pyrrolidone (NVP) and DMA. Replacing a substantial portion of the silicone macromer with TRIS reduced the modulus of the resulting hydrogels. Two publications from the same author, "The Role of Bulky Polysiloxanylalkyl Methacrylates in Polyurethane-Polysiloxane Hydrogels", *J. Appl. Poly. Sci.*, Vol. 60, 1193-1199 (1996), and "The Role of Bulky Polysiloxanylalkyl Methacrylates in Oxygen-Permeable Hydrogel Materials", *J. Appl. Poly. Sci.*, Vol. 56, 317-324 (1995) also describe experimental results indicating that the modulus of hydrogels made from reaction mixtures of silicone-macromers and hydrophilic monomers such as DMA decreases with added TRIS. The addition of methacryloxypropyltris(trimethylsiloxy)silane (TRIS) reduced the modulus of such hydrogels, but in many examples the modulus was still higher than may be desired.

U.S. Pat. No. 4,208,506 describes monomeric polyparaffinsiloxanes end-capped with activated unsaturated groups and polymers and copolymers thereof. The monomers of U.S. Pat. No. 4,208,506 are cross-linkers. We have discovered that mono ethylenically unsaturated polycarbosiloxane monomers are advantageous in device forming monomer mixes because in addition to reducing the crosslink density of the polymerized mixture the additional chain length of the alkyl portion of the monomer backbone reduces the modulus of the polymerized monomer mix.

There still remains a need in the art for silicone hydrogels which are soft enough to make soft contact lenses, which possess high oxygen permeability, suitable water content, and sufficient elasticity, and are comfortable to the contact lens wearer.

BRIEF DESCRIPTION OF THE DRAWINGS

None.

DETAILED DESCRIPTION

Unless clearly stated otherwise all materials used in forming a monomer mix are listed as weight percent. Also, unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

In a first aspect, the invention relates to monomers of formula (I):

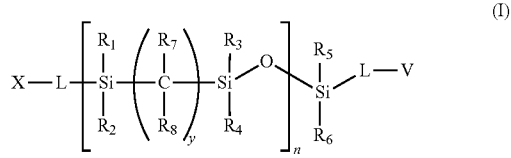

wherein X is the residue of a ring opening agent; L is the same or different and is a linker group or a bond; V is an ethylenically unsaturated polymerizable group; $R_1$, $R_2$, $R_3$, $R_4$, $R_5$, $R_6$ are independently H, alkyl, halo alkyl, cyclo alkyl, heterocyclo alkyl, alkenyl, halo alkenyl, or aromatic; $R_7$ and $R_8$ are independently H or alkyl wherein at least one of $R_7$ or $R_8$ is hydrogen; y is 2-7 and n is 1-100.

Ring opening agents are well known in the literature. Non-limiting examples of anionic ring opening agents include alkyl lithiums, alkoxides, trialkylsiloxylithium wherein the alkyl group may or may not contain halo atoms.

Linker groups can be any divalent radical or moiety and include substituted or unsubstituted alkyl, alkyl ether, alkenyls, alkenyl ethers, halo alkyls, substituted or unsubstituted siloxanes, and monomers capable of propagating ring opening.

Ethylenically unsaturated polymerizable groups are well known to those skilled in the art. Non-limiting examples of ethylenically unsaturated polymerizable groups would include acrylates, methacrylates, vinyl carbonates, O-vinyl carbamates, N-vinyl carbamates, acrylamides and methacrylamides.

Additional preferred embodiments of the monomers of the invention herein would include monomers of formula (II):

(II)

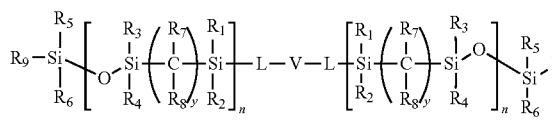

wherein L is the same or different and is a linker group or a bond; V is the same or different and is an ethylenically unsaturated polymerizable group; $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic; $R_7$ and $R_8$ are independently H or alkyl wherein at least one of $R_7$ or $R_8$ is hydrogen; y is 2-7 and n is 1-100.

Additional preferred embodiments of the monomers of the invention herein would include monomers of the following formulas III and IV:

(III)

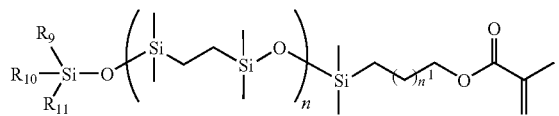

wherein $R_9$, $R_{10}$ and $R_{11}$ are independently H, alkyl, haloalkyl or other substituted alkyl groups; n is as defined above and $n^1$ is 0-10; and, (IV)

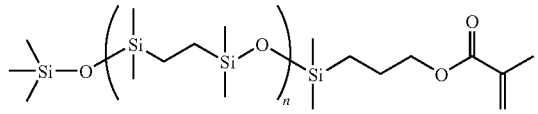

wherein n is 1-100, preferably n is 2-80, more preferably n is 3-20, most preferably n is 5-15.

Additional preferred embodiments of the monomers of the invention herein would include monomers of the following formulas V-IX:

(M1-EDS6-TMS)

(V)

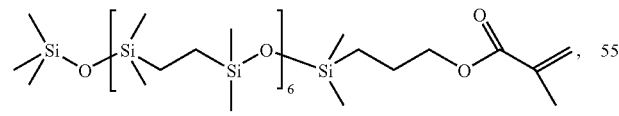

(M1-EDS7-TMS)

(VI)

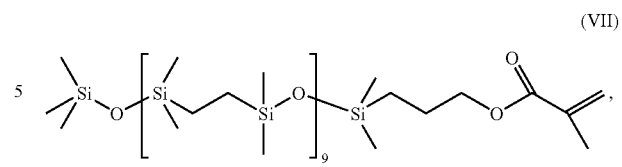

(M1-EDS9-TMS)

(VII)

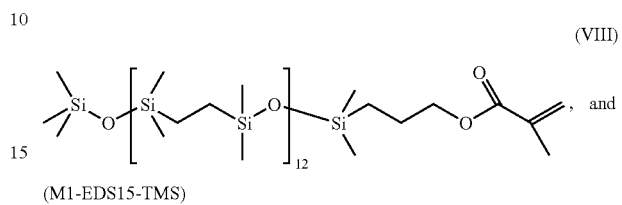

(M1-EDS12-TMS)

(VIII)

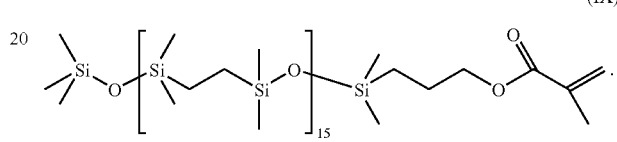

(M1-EDS15-TMS)

(IX)

Additional preferred embodiments of the monomers of the invention herein would include monomers of the following formulas X-XII:

(X)

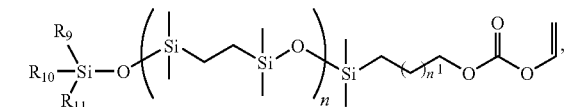

(XI)

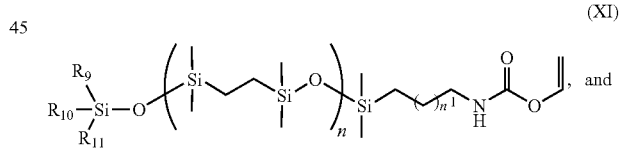

(XII)

wherein $R_9$, $R_{10}$ and $R_{11}$ are independently H, alkyl, haloalkyl or other substituted alkyl groups and n and $n^1$ are as defined above.

Additional preferred embodiments of the monomers of the invention herein would include monomers of the following formulas XIII-XV:

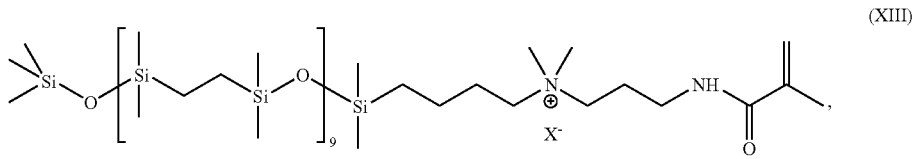
(XIII)

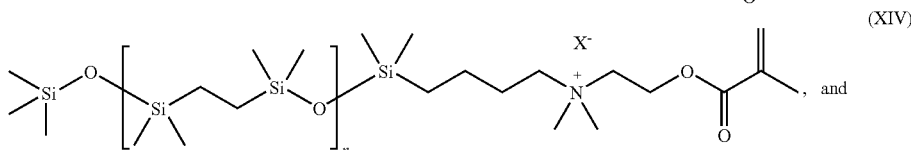
(XIV), and

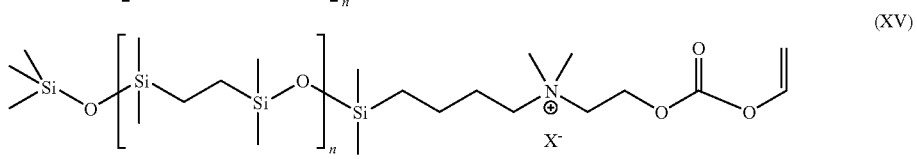
(XV)

wherein n is as defined above and $X^-$ is a counterion to provide an overall neutral charge.

Counterions capable of providing an overall neutral charge are well known to those of ordinary skill in the art and would include, for example, halide ions.

An additional preferred embodiment of the monomers of the invention herein would include the monomer of the following formula XVI:

(M1-EDS7-D37-TMS)

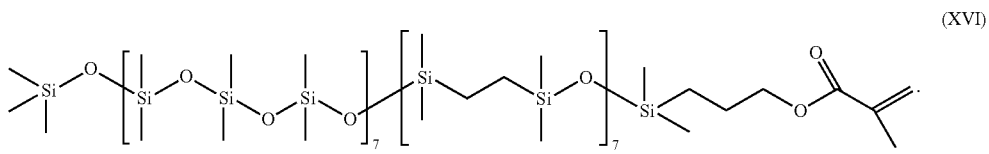
(XVI)

Monomers of formula I can be prepared by various synthetic methods, for example:

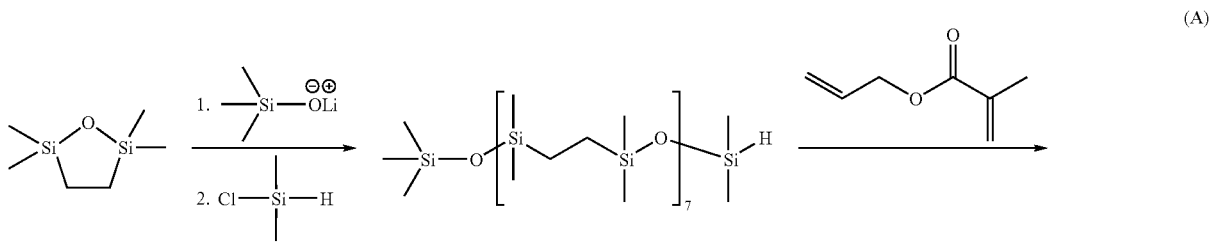
(A)

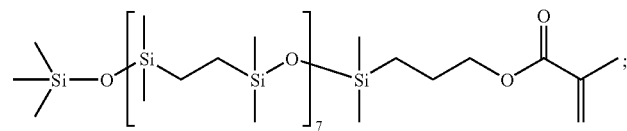

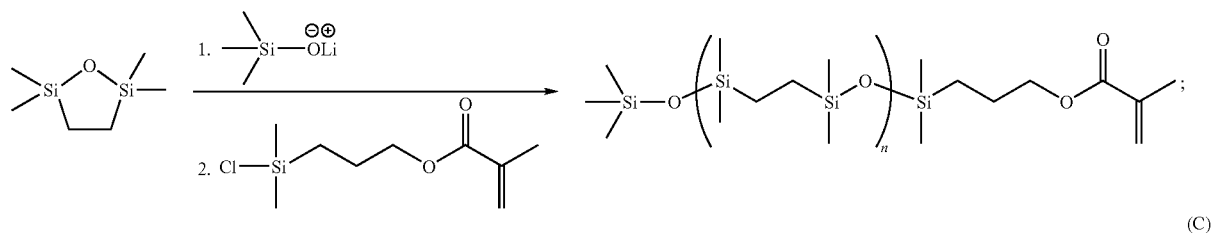

(B)

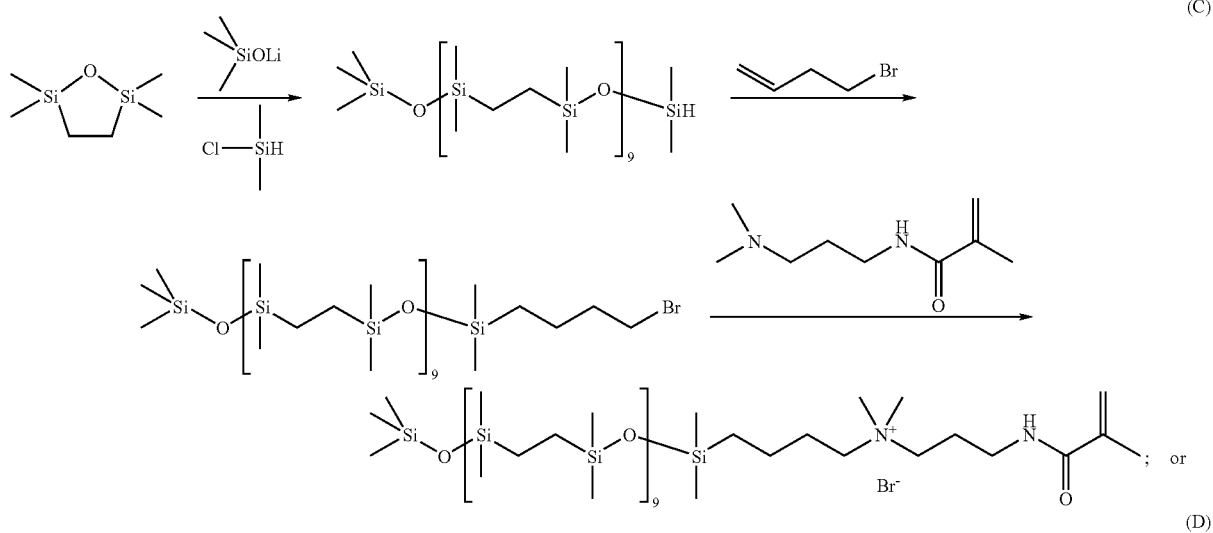

(C)

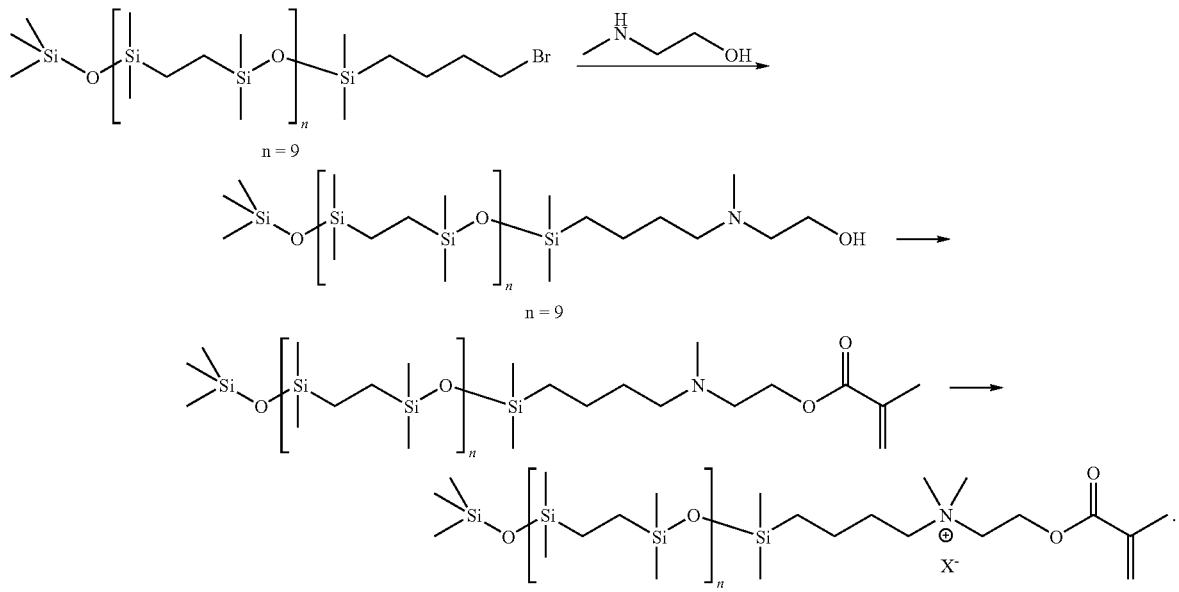

(D)

Monomers of formula II can be prepared by various synthetic methods, for example as shown in Example 6.

The term "monomer" used herein refers to varying molecular weight compounds (i.e. typically having number average molecular weights from about 700 to about 100,000) that can be polymerized, and to medium to high molecular weight compounds or polymers, sometimes referred to as macromonomers, (i.e., typically having number average molecular weights greater than 700) containing functional groups capable of further polymerization. Thus, it is understood that the terms "organosilicon-containing monomers", "silicone-containing monomers" and "hydrophilic monomers" include monomers, macromonomers and prepolymers. Prepolymers are partially polymerized monomers or monomers which are capable of further polymerization.

An "organosilicon-containing monomer" contains at least one [—Si—O—] or at least one [—Si—($C_2$-$C_7$ alkyl)—Si—O—] repeating units, in a monomer, macromer or prepolymer. Preferably, the total Si and attached O are present in the organosilicon-containing monomer in an amount greater than 5 weight percent, and more preferable greater than 30 weight percent of the total molecular weight of the organosilicon-containing monomer. A "silicone-containing monomer" is one that contains at least one [—Si—O—] repeating units, in a monomer, macromer or prepolymer.

In yet another aspect, the invention includes articles formed of device forming monomer mixes comprising, alone or in combination, any of the monomers of formulas I-XVI. According to preferred embodiments, the article is the polymerization product of a mixture comprising at least one of the aforementioned monomers of formulas I-XVI and at least a second copolymerizable monomer. The invention is applicable to a wide variety of polymeric materials, either rigid or soft. Especially preferred polymeric materials are lenses including contact lenses, phakic and aphakic intraocular lenses and corneal implants although all polymeric materials including biomaterials are contemplated as being within the scope of this invention. Preferred articles are optically clear and useful as a contact lens.

The monomer mix of the present invention also provides medical devices such as artificial heart valves, films, surgical devices, vessel substitutes, intrauterine devices, membranes, diaphragms, surgical implants, artificial blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially hydrogel contact lenses.

Unless clearly stated otherwise it will be understood that all amounts of materials used to make the monomers and monomer mixes disclosed herein represent the statistical mean of a normal distribution of weight values such as are ordinarily encountered in the laboratory or commercial manufacture of the monomers and monomer mixes disclosed herein. Therefore, unless clearly stated otherwise, all numerical values shall be understood as being modified by the term "about".

Useful concentration of the mono ethylenically unsaturated polycarbosiloxane monomers of the invention herein would be 0.1 to 30 percent by weight of the monomer mix. More preferred concentrations are 0.1 to 20 percent by weight. Even more preferred concentrations would be 5 to 15 percent by weight.

Preferred compositions have both hydrophilic and hydrophobic monomers. Depending upon the specific application, useful articles made with these materials may require additional (other than the subject mono ethylenically unsaturated polycarbosiloxane monomers) hydrophobic, possibly silicone containing monomers. These additional silicone containing hydrophobic monomers will be present at between 0.1 to 75.8 percent by weight, more preferably between 2 to 20 percent by weight, even more preferably between 5 to 13 percent by weight. Amounts of non-silicone containing hydrophobic monomers will be 0 to 60 percent by weight. Examples of non-silicone hydrophobic materials include alkyl acrylates and methacrylates. Especially preferred is silicone-containing hydrogels.

Depending upon the application, useful articles may also require bulky monomers such as those disclosed in U.S. Pat. No. 6,921,802 which include methacryloxypropyl tris(trimethylsiloxy)silane ("TRIS"), pentamethyldisiloxanyl methylmethacrylate, tris(trimethylsiloxy)methacryloxy propylsilane, phenyltretramethyl-disloxanylethyl acrylate, methyldi(trimethylsiloxy)methacryloxymethyl silane, 3-[tris(trimethylsiloxy)silyl]propyl vinyl carbamate, 3[tris(trimethylsiloxy)silyl]propyol allyl carbamate, and 3-[tris(trimethylsiloxy)silyl]propyl vinyl carbonate. These bulky monomers, when present, may be present at 0 to 41.2 percent by weight, 34 to 41 percent by weight or even 25 to 41 percent by weight.

Silicone-containing hydrogels are prepared by polymerizing a mixture containing at least one silicone-containing monomer and at least one hydrophilic monomer. The silicone-containing monomer may function as a crosslinking agent (a crosslinker being defined as a monomer having multiple polymerizable functionalities) or a separate crosslinker may be employed. Hydrophobic crosslinkers would include methacrylates such as ethylene glycol dimethacrylate (EGDMA) and allyl methacrylate (AMA). Amounts of crosslinker would be between 0 to 76 percent by weight, 2 to 20 percent by weight or 5 to 13 percent by weight.

The mono ethylenically unsaturated polycarbosiloxane monomers of the invention herein may be copolymerized with a wide variety of hydrophilic monomers to produce silicone hydrogel lenses. Suitable hydrophilic monomers include: unsaturated carboxylic acids, such as methacrylic and acrylic acids; acrylic substituted alcohols, such as 2-hydroxyethyl methacrylate and 2-hydroxyethyl acrylate; vinyl lactams, such as N-vinylpyrrolidone (NVP) and 1-vinylazonan-2-one; and acrylamides, such as methacrylamide and N,N-dimethylacrylamide (DMA). These hydrophilic monomers will be present, separately or by combined weight in amounts of between 0 to 60 percent by weight, between 20 to 45 percent by weight, between 0 to 48.6 percent by weight, between 0 to 30 percent by weight, between 0 to 25 percent by weight, between 0 to 9.5 percent by weight or between 2 to 7 percent by weight.

Other examples of silicone-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al.); fumarate monomer mixtures as disclosed in U.S. Pat. Nos. 5,374,662; 5,420,324 and 5,496,871 (Lai et al.) and urethane monomer mixtures as disclosed in U.S. Pat. Nos. 5,451,651; 5,648,515; 5,639,908 and 5,594,085(Lai et al.), all of which are commonly assigned to assignee herein Bausch & Lomb Incorporated, and the entire disclosures of which are incorporated herein by reference. Other suitable hydrophilic monomers will be apparent to one skilled in the art.

An organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include alcohols such as tert-butanol (TBA), tert-amyl alcohol, hexanol and nonanol; diols, such as ethylene glycol; and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect (for example, minimal phase separation of polymerized products). Generally, the diluent is included at 0 to 60% by weight of the monomeric mixture, with 1 to 40% by weight being more preferred, 2 to 30% by weight being even more preferred and 3 to 25% by weight being especially preferred.

According to the present process, the monomeric mixture, comprising at least one hydrophilic monomer, at least one mono ethylenically unsaturated polycarbosiloxane monomer and optionally the organic diluent, is shaped and cured by conventional methods such as static casting or spincasting.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photoinitiation of polymerization of the monomer mixture as is well known in the art may also be used in the process of forming an article as disclosed herein. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Therefore, once the biomaterials formed from the polymerized monomer mix containing the monomers disclosed herein are formed they are then extracted to prepare them for packaging and eventual use. Extraction is accomplished by exposing the polymerized materials to various solvents such as water, 2-propanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water or buffer solution.

Following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

The following examples are provided to enable one skilled in the art to practice the invention and are merely illustrative of the invention. The examples should not be read as limiting the scope of the invention as defined in the claims.

EXAMPLES

All solvents and reagents were obtained from commercially available sources and used as received.
Analytical Measurements
ESI-TOF MS: The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution. For exact mass measurements poly(ethylene glycol) (PEG), having a nominal Mn value of 400 Da, was added to the sample of interest and used as an internal mass standard. Two PEG oligomers that bracketed the sample mass of interest were used to calibrate the mass scale. Samples were prepared as 30 µM solutions in isopropanol (IPA) with the addition of 2% by volume saturated NaCl in IPA. Samples were directly infused into the ESI-TOF MS instrument at a rate of 35µL/min. A sufficient resolving power (6000 RP m/AΔm FWHM) was achieved in the analysis to obtain the monoisotopic mass for each sample. In each analysis the experimental monoisotopic mass was compared to the theoretical monoisotopic mass as determined from the respective elemental compositions. In each analysis the monoisotopic mass comparison was less than 10 ppm error. It should be noted that uncharged samples have a sodium (Na) atom included in their elemental composition. This Na atom occurs as a necessary charge agent added in the sample preparation procedure. Some samples do not require an added charge agent since they contain a charge from the quaternary nitrogen inherent to their respective structure.

GC: Gas chromatography was performed using a Hewlett Packard HP 6890 Series GC System. Purities were determined by integration of the primary peak and comparison to the normalized chromatograph.

NMR: $^1$H-NMR characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

Mechanical properties and Oxygen Perneability: Modulus and elongation tests were conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) was determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an 02 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, *Optom Vis Sci* 7 (12s): 95 (1997), the disclosure of which is incorporated herein in its entirety:

| MATERIAL NAME | REPOSITORY VALUES | LOWER LIMIT | UPPER LIMIT |
|---|---|---|---|
| Fluoroperm 30 | 26.2 | 24 | 29 |
| Menicon EX | 62.4 | 56 | 66 |
| Quantum II | 92.9 | 85 | 101 |

Abbreviations:
NVP 1-Vinyl-2-pyrrolidone
TRIS 3-Methacryloxypropyltris(trimethylsiloxy)silane
HEMA 2-Hydroxyethyl methacrylate
v-64 2,2'-Azobis(2-methylpropionitrile)
EGDMA ethylene glycol dimethacrylate Unless otherwise specifically stated or made clear by its usage, all numbers used in the examples should be considered to be modified by the term "about" and to be weight percent.

General Synthetic Scheme for M1-(EDS)$_n$- TMS

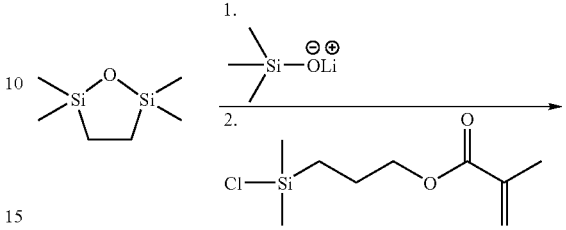

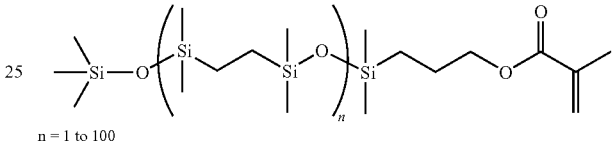

$n = 1$ to $100$

Ma2D37

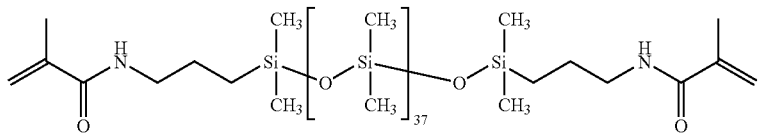

Molecular Weight = 3128.43
Molecular Formula = $C_{92}H_{258}N_2O_{40}Si_{39}$

VI-MCR-C12

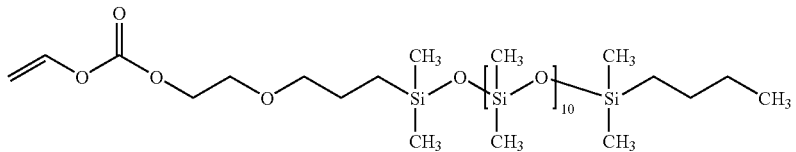

Vca-MCR-C12 or (Va-MCR-C12)

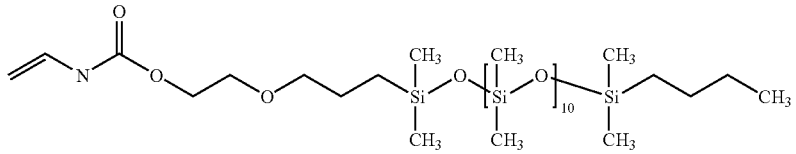

Example 1

Synthesis of M1-EDS7-TMS

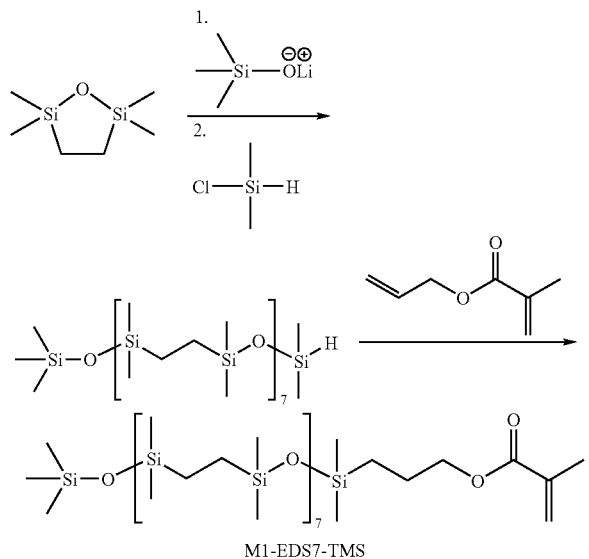

2,2,5,5-tetramethyl-2,5-disila-1-oxacyclopentane (19.2 g, 0.12 mol) was taken in 50 mL of dry cyclohexane under N₂ and stirred for 30 min at 25° C. To this mixture lithium trimethylsilanolate (1.92 g, 0.02 mol) was added with stirring. After 1 h dry THF (25 mL) was added and the reaction mixture continued to stir for 24 h at 25° C. Dimethylchlorosilane (1.9 g, 0.02 mol) was then added and the color change was observed. Stirring was continued for 3 h more and the reaction mixture was then filtered. Filtrate was concentrated under vacuum to give clear oil in 22 g yield as the expected product based on the method of preparation and characterized by NMR, SEC and MALDI showing about 7 condensed 2,2,5,5-tetramethyl-2,5-disila-1-oxacyclopentane ring open units. It was used as such for hydrosilation by taking into toluene (20 mL) and adding allylmethacrylate (3.15 g, 0.025 mol, 25 mmol) under N₂ atmosphere followed by the addition of platinum(0)1,3-divinyl-1,1,3,3-tetramethyl disiloxane complex 3 wt % solution in xylene (as catalyst). The reaction mixture was stirred for 6 h at 40-45° C. Stripping of the solvent on roto-vap and then high vacuum to gave an yellow oil in 17 g yield as the desired product characterized by MALDI.

Example 2

Synthesis of M1-EDS6-TMS

To an oven dried 2 L two-neck round bottom flask equipped with a magnetic stirring bar and condenser under N2 atmosphere were added 2,2,5,5-tetramethyl-2,5-disila-1-oxacyclopentane (77.22 g, 0.482 mol) and anhydrous cyclohexane (150 mL) under stirring in N2 atmosphere. Lithium trimethyl silanolate (7.2 g, 0.0749 mol) was added to the above reaction mixture followed by the addition of cyclohexane (25 mL). After stirring for one hour, THF (70 mL, distilled over Na/Benzophenone) was added and the reaction mixture continued to stir for 16 hours. Methylacryloxypropyl dimethylchlorosilane (20 g, 0.09 mol) was then added and the mixture stirred for another 24 hours. Reaction mixture was then filtered and Silica gel (3.5 g, dried at 160° C. for 3 hours) was then added and the reaction mixture stirred another 4 hour. Reaction mixture was then filtered thru a bed of Celite (20 g) and BHT (5 mg) was added to the filtrate. The filtrate was then concentrated under vacuum (40° C./0.3 mm Hg). Heptane (200 mL) was then added to the concentrate with shaking and washed with DI water (100 mL), aqueous NaHCO3 (2×100 mL, prepared by dissolving 10 g NaHCO3 in 200 mL DI water), brine (100 mL) and finally DI water (100 mL). Heptane (50 mL) was then added and dried over MgSO4 (15 g) for 20 hours. MgSO4 was filtered off and the solvent was removed on rotary evaporator. The crude product was stirred over activated basic Alumina (30 g for 24 h) and then filtered over a thin bed of celite Stripping off any residue solvent at 25° C. at 0.2 mmHg for 30 minutes yielded the desired product as a clear oil in 80 g quantity. It was characterized by NMR, GPC, GC-MS and MALDI.

Example 3

Synthesis of M1-EDS9-TMS 2,2,5,5-tetramethyl-2,5-disila-1-oxacyclopentane (14.4 g, 0.09 mol) was taken in 35 mL of dry cyclohexane under N₂ and stirred for 10 min at 25° C. To this lithium trimethylsilanolate (960 mg, 0.01 mol) was added with stirring. After 2 h dry THF (20 mL) was added and the reaction mixture continued to stir for 24 h at 25° C. Chlorodimethylsilylpropyloxy methacrylate (2.20 g, 0.01 mol) was then added and the color change was observed. Stirring was continued for 24 h more and the reaction mixture was then quenched with 10 mg NaHCO₃. Cyclohexane (10 mL) was added with continued stirring for 2 h more. Reaction mixture was then filtered over Celite. Filtrate was concentrated under vacuum to give clear oil in 16 g yield as the expected product based on the method of preparation and characterized by NMR, SEC and MALDI showing about 9 condensed 2,2,5,5-tetramethyl-2,5-disila-1-oxacyclopentane ring open units.

Example 4

Synthesis of M1-EDS12-TMS 2,2,5,5-tetramethyl-2,5-disila-1-oxacyclopentane (19.2 g, 0.12 mol) was taken in 50 mL of dry cyclohexane under N₂ and stirred for 30 min at 25° C. To this lithium trimethylsilanolate (960 mg, 0.01 mol) was added with stirring. After 2 h dry THF (20 mL) was added and the reaction mixture continued to stir for 24 h at 25° C. Chlorodimethylsilylpropyloxy methacrylate (2.20 g, 0.01 mol) was then added and the color change was observed. Stirring was continued for 24 h more and the reaction mixture was then filtered over Celite. Filtrate was concentrated under vacuum to give clear oil in 20 g yield as the expected product based on the method of preparation and characterized by NMR, SEC and MALDI showing about 12 condensed 2,2,5,5-tetramethyl-2,5-disila-1-oxacyclopentane ring open units.

Example 5

Synthesis of M1-EDS15-TMS 2,2,5,5-tetramethyl-2,5-disila-1-oxacyclopentane (24 g, 0.15 mol) was taken in 60 mL of dry cyclohexane under N₂ and stirred for 10 min at 25° C. To this lithium trimethylsilanolate (960 mg, 0.01 mol) was added with stirring. After 2 h dry THF (20 mL) was added and the reaction mixture continued to stir for 24 h at 25° C. Chlorodimethylsilylpropyloxy methacrylate (2.20 g, 0.01 mol) was then added and the color change was observed. Stirring was continued for 24 h more and the reaction mixture was then quenched with 10 mg NaHCO₃. Cyclohexane (10 mL) was added with continued stirring for 2 h more. Reaction mixture was then filtered over Celite. Filtrate was concentrated under vacuum to give clear oil in 25 g yield as the expected product based on the method of preparation and characterized by NMR, SEC and MALDI showing about 15 condensed 2,2,5,5-tetramethyl-2,5-disila-1-oxacyclopentane ring open units.

Example 6

Synthesis of M1-BIS-EDS3-TMS

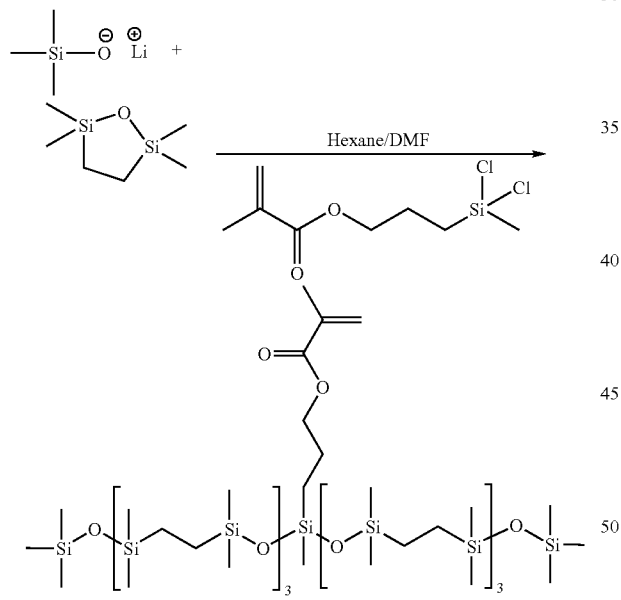

Lithium trimethyl silanolate (19.7 g, 0.2 mol) was suspended in anhydrous hexane (100 mL) in a 500 mL, round bottom flask was fitted with a mechanical stirrer, argon gas and a dropping funnel. A solution of 2,2,5,5-tetramethyl-2,5-disila-1-oxacyclopentane (32.07 g, 0.2 mol) in anhydrous hexane (100 mL), was quickly added to the flask with stirring. After an hour, the flask was cooled with an ice bath and DMF (50 mL) was added with continued stirring. After 4 h, 3-methacryloxypropyl methyldichlorosilane (29 g, 0.12 mol) was added dropwise to the reaction mixture. The reaction mixture was stirred further 24 h at room temperature. Deionized water (50 mL) was then added to the flask with stirred. The organic layer was separated and dried over anhydrous sodium sulfate and filtered. The solvent was evaporated on a roto-vap to give the desired product in 40 g quantity as a clear, yellowish oil. The product was characterized by GC, GC/MS, IR and NMR.

Example 7

Synthesis of Dimethylammonium Methacrylamide (MA1-Q-EDS9-TMS)

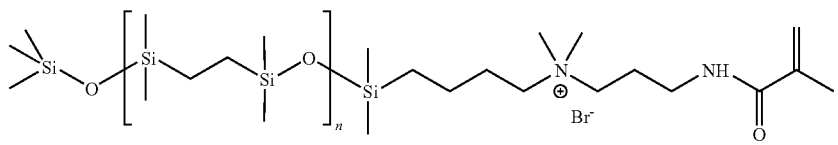

wherein n is as defined above.

2,2,5,5-tetramethyl-2,5-disila-1-oxacyclopentane (48 g, 0.3 mol) was taken in 55 mL of dry cyclohexane under N₂ and stirred for 30 min at 25° C. To this lithium trimethylsilanolate (4.8 g, 0.05 mol) was added with stirring. After 1 h dry THF (25 mL) was added and the reaction mixture continued to stir for 24 h at 25° C. Dimethylchlorosilane (5.1 g, 0.55 mol) was then added and the color change was observed. Stirring was continued for 3 h more and the reaction mixture was then filtered. Filtrate was concentrated under vacuum to give clear oil in 42 g yield as the expected product based on the method of preparation and characterized by NMR, SEC and MALDI. 28.0 g of this was used for hydrosilation by taking into toluene (30 mL) and adding 1-bromobutene (4 g, 0.03 mol,) under N₂ atmosphere followed by the addition of platinum(0)1,3-divinyl-1,1,3,3-tetramethyl disiloxane complex 3 wt % solution in xylene (100 uL as catalyst). The reaction mixture was stirred for 4 h at 45-50° C. and then at 25° C. for 48 h. The reaction mixture was filtered over Celite using cotton plug. Stripping of the solvent on roto-vap and then high vacuum to gave an yellow oil in 27 g yield as the desired bromo compound characterized by MALDI with n=~9 units.

6.6 g (0.004 mol) of the bromo compound and 680 mg (0.004 mol) of dimethylaminopropyl methacrylamide were mixed together and stirred under N2 for 6 h at 25° C. Some exotherm was observed. Reaction mixture was subjected to high vacuum after 10 h to give the desired product in almost quantitative yield and characterized by NMR and MALDI.

Example 8

Synthesis of Comparative Monofunctional M1-MCR-C12

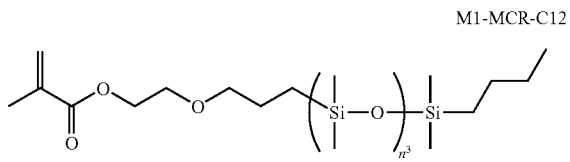

M1-MCR-C12 wherein n³ is as defined above

Hydroxy ethoxypropyl terminated polydimethylsiloxane (50 grams, 0.048 mol) available from Gelest, Inc. (MCR-C12) was added to a 500 mL round bottom flask and dried via azeotropic distillation of toluene. To the flask was added anhydrous methylene chloride (200 mL) and triethylamine (17.12 g, 0.17 mol) and the reaction was stirred for 20 minutes. The reaction flask was fitted with an addition funnel which was charged with methacryloyl chloride (17.18 g, 0.16 mol) and an additional 85 mL of anhydrous methylene chloride. The contents of the addition funnel were added to the reaction mixture dropwise at which time the addition funnel was exchanged with a reflux condenser. The reaction was then brought to reflux for 4 hours. After cooling the reaction mixture was filtered and placed in a separatory funnel where it was washed with 2 times 0.1 N HCl (150 mL); 2 times sodium bicarbonate solution (150 mL) and 2 times Brine solution (150 mL). The organic layer was then stirred with 10 grams of decolorizing carbon and 10 grams of silica gel for 24 hours and was then filtered and brought to dryness on a roto-vap. The reaction yielded 45 g of a clear, yellow oil that was characterized by GC, NMR, and MALDI.

Example 9

Synthesis of Comparative Monofunctional MCA1-MCR-C12

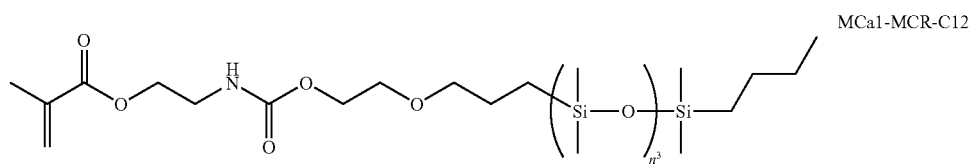

wherein $n^3$ is as defined above.

Hydroxy ethoxypropyl terminated polydimethylsiloxane (200 grams, 0.193 mol) available from Gelest, Inc. (MCR-C12) was added to a 2 L round bottom flask and dried via azeotropic distillation of toluene. To the flask was added anhydrous methylene chloride (500 mL) and dibutyltin dilaurate (0.474 g, 0.0007 mol). The reaction flask was fitted with an addition funnel which was charged with 2-Isocyanatoethyl methacrylate (45.0 g, 0.290 mol) and an additional 100 mL of anhydrous methylene chloride. The contents of the addition funnel were added to the reaction mixture dropwise and the reaction then stirred for 48 hours. 50 grams of silica gel (EMD Silica gel 60) are then added to the reaction and stirred for 24 hours to scavenge excess isocyanatoethyl methacrylate. The reaction is then filtered and concentrated on a roto-vap yielding 210 g of a clear oil that was characterized by GC, NMR, and MALDI.

TABLE 1

Examples 10-23. Formulation of various EDS based monomers and comparative examples

| Example | Ma2D37 Methacrylamide Crosslinker | TRIS [tris(trimethylsiloxy)-silylpropyl methacrylate] | N-Vinyl Pyrolidone | N,N-Dimethylacrylamide | 2-Hydroxyethyl methacrylate | Hexanol | M1-MCR-C12 |
|---|---|---|---|---|---|---|---|
| 10 | 9.5 | 35.5 | 30.8 | 4.7 | 4.7 | 4.7 | 9.5 |
| 11 | 9.5 | 35.5 | 30.8 | 4.7 | 4.7 | 4.7 | x |
| 12 | 9.5 | 35.5 | 30.8 | 4.7 | 4.7 | 4.7 | x |
| 13 | 9.5 | 35.5 | 30.8 | 4.7 | 4.7 | 4.7 | x |
| 14 | 9.5 | 35.5 | 30.8 | 4.7 | 4.7 | 4.7 | x |
| 15 | 9.5 | 35.5 | 30.8 | 4.7 | 4.7 | 4.7 | x |
| 16 | 9.5 | 35.5 | 30.8 | 4.7 | 4.7 | 4.7 | x |
| 17 | 0.0 | 29.9 | 25.9 | 4.0 | 4.0 | 19.9 | x |
| 18 | 0.0 | 32.5 | 28.1 | 4.3 | 4.3 | 13.0 | x |
| 19 | 9.5 | 35.5 | 30.8 | 4.7 | 4.7 | 4.7 | x |
| 20 | 9.5 | 35.5 | 30.8 | 4.7 | 4.7 | 4.7 | x |
| 21 | 9.5 | 35.5 | 30.8 | 4.7 | 4.7 | 4.7 | x |
| 22 | 9.5 | 35.5 | 30.8 | 4.7 | 4.7 | 4.7 | x |
| 23 | 9.5 | 35.5 | 30.8 | 4.7 | 4.7 | 4.7 | x |

| Example | MCa1-MCR-C12 | M1-EDS7-TMS | M1-EDS6-TMS | M1-EDS9-TMS | M1-EDS12-TMS | M1-EDS15-TMS | M2-EDS23 | M2-D27-EDS10 |
|---|---|---|---|---|---|---|---|---|
| 10 | x | x | x | x | x | x | x | x |
| 11 | 9.5 | x | x | x | x | x | x | x |
| 12 | x | 9.5 | x | x | x | x | x | x |
| 13 | x | x | 9.5 | x | x | x | x | x |
| 14 | x | x | x | 9.5 | x | x | x | x |
| 15 | x | x | x | x | 9.5 | x | x | x |
| 16 | x | x | x | x | x | 9.5 | x | x |
| 17 | x | x | x | 8.0 | x | x | 8.0 | x |
| 18 | x | x | x | 8.7 | x | x | x | 8.7 |

TABLE 1-continued

Examples 10-23. Formulation of various EDS based monomers and comparative examples

| | | | | | | | | |
|---|---|---|---|---|---|---|---|---|
| 19 | x | x | x | x | x | x | x | x |
| 20 | x | x | x | x | x | x | x | x |
| 21 | x | x | x | x | x | x | x | x |
| 22 | x | x | x | x | x | x | x | x |
| 23 | x | x | x | x | x | x | x | x |

| Example | M1-Bis-D3-TMS | M1-Bis-EDS3-TMS | Ma1-Q-EDS9-TMS | V1-MCR-C12 | VCa1-MCR-C12 | Darocur 1173 | IMVT (concentration in ppm) |
|---|---|---|---|---|---|---|---|
| 10 | x | x | x | x | x | 0.47 | 90 |
| 11 | x | x | x | x | x | 0.47 | 90 |
| 12 | x | x | x | x | x | 0.47 | 90 |
| 13 | x | x | x | x | x | 0.47 | 90 |
| 14 | x | x | x | x | x | 0.47 | 90 |
| 15 | x | x | x | x | x | 0.47 | 90 |
| 16 | x | x | x | x | x | 0.47 | 90 |
| 17 | x | x | x | x | x | 0.47 | 90 |
| 18 | x | x | x | x | x | 0.47 | 90 |
| 19 | 9.5 | x | x | x | x | 0.47 | 90 |
| 20 | x | 9.5 | x | x | x | 0.47 | 90 |
| 21 | x | x | 9.5 | x | x | 0.47 | 90 |
| 22 | x | x | x | 9.5 | x | 0.47 | 90 |
| 23 | x | x | x | x | 9.5 | 0.47 | 90 |

Note:
The amounts presented in the table above are weight percentages in the formulation.
Tint level is in ppm.

Preparation Procedure:

For examples 10-15, 17-23, 32, 54-56 and 69, the specific monomer mixes set forth were prepared according to the table 1 above and tables 3 and 5 below by weighing out various weight percentages of the components. Monomer mix was dispensed between polypropylene molds and prepared as lenses or flats in the case of Dk samples. Polymerization was carried out under UV light (~350 nm) for a period of two hours. After polymerization, the lenses or flats were released from the molds using 33% IPA in water and then extracted in 100% IPA for 4 hours. Lenses/Flats were then placed in deionized water for 30 minutes and packaged in vials containing 4 mL of borate buffered saline (BBS). Measured properties for the lenses/flats are shown in the table below.

A 4502 Mechanical Tester MTS Instron was used to measure the modulus, tensile strength, percent elongation and tear strength of the lenses. Samples were tested in a water bath containing borate buffered saline.

Captive bubble contact angle data was collected on a First Ten Angstroms FTA-1000 Drop Shape Instrument. All samples were rinsed in HPLC grade water prior to analysis in order to remove components of the packaging solution from the sample surface. Prior to data collection the surface tension of the water used for all experiments was measured using the pendant drop method. In order for the water to qualify as appropriate for use, a surface tension value of 70-72 dynes/cm was expected. All lens samples were placed onto a curved sample holder and submerged into a quartz cell filled with

TABLE 2

Selected Properties of processed lenses/flats containing EDS monomers and comparative examples.

| Example | Water Content (%) | Dk (barrers) | Modulus (gm/sqmm) | Elongation (%) | Tear Strength (gm/mm) | Advancing Contact Angle | Receding Contact Angle | Hysteressis |
|---|---|---|---|---|---|---|---|---|
| 10 | 42.3 | 96 | 92 (10) | 125 (52) | 7 (1) | 28 (4) | 19 (0) | 9 (4) |
| 11 | 43.0 | x | 107 (10) | 100 (30) | 4 (1) | 29 (2) | 21 (1) | 8 (1) |
| 12 | 47.3 | 93 | 58 (6) | 100 (30) | 4 (1) | 29 (2) | 21 (1) | 8 (1) |
| 13 | 40.8 | 87 | 91 (9) | 177 (25) | 5 (1) | 29 (3) | 21 (3) | 8 (6) |
| 14 | 42.1 | x | .3/17 | .3/17 | .3/17 | x | x | x |
| 15 | 35.7 | x | .3/17 | .3/17 | .3/17 | x | x | x |
| 16 | ND | ND | ND | ND | ND | ND | ND | ND |
| 17 | 42.0 | 95 | 74 (4) | 236 (25) | 7 (1) | x | x | x |
| 18 | 41.6 | 85 | 66 (5) | 143 (43) | 6 (1) | | | |
| 19 | 40.9 | x | 137 (6) | 157 (22) | x | x | x | x |
| 20 | 32.0 | x | 137 (8) | 137 (20) | x | x | x | x |
| 21 | 43.1 | x | 140 (6) | 96 (14) | x | x | x | x |
| 22 | 41.9 | x | 98 (10) | 159 (29) | 6 (0.4) | 98 (2) | 21 (1) | 76 (1) |
| 23 | 39.2 | x | 105 (5) | 125 (23) | 5 (1) | 96 (5) | 21 (1) | 76 (5) |
| 32 | 46.9 | 91 | 71 (8) | 165 (74) | x | 31 (6) | 16 (1) | 15 (5) |
| 54 | 44.9 | x | 84 (10) | 177 (31) | 4 (1) | 33 (0.7) | 19 (1.0) | 14 (1.6) |
| 55 | 43.2 | x | 80 (7) | 176 (60) | 7 (1) | 40 (7.0) | 24 (2.3) | 16 (9.2) |
| 56 | 43.3 | x | 72 (4) | 159 (68) | 7 (0.3) | 41 (2.0) | 22 (1.4) | 19 (0.6) |
| 69 | 32.0 | x | 137 (8) | 137 (20) | x | x | x | x |

HPLC grade water. Receding and advancing captive bubble contact angles were collected for each sample. The receding contact angle is defined as the angle measured in water as the air bubble is expanding across the sample surface (water is receding from the surface). The advancing contact angle is defined as the angle measured in water as the air bubble is retracting from the lens surface (water is advancing across the surface). All captive bubble data was collected using a high speed digital camera focused onto the sample/air bubble interface. The contact angle was calculated at the digital frame just prior to contact line movement across the sample/air bubble interface.

TABLE 3

Further examples of monomer mix formulations.

| Example | Ma2D37 Methacrylamide Crosslinker | TRIS [tris(trimethylsiloxy)-silylpropyl methacrylate] | N-Vinyl Pyrolidone | N,N-Dimethylacrylamide | 2-Hydroxyethyl methacrylate | Hexanol | M1-EDS6-TMS | Darocur 1173 | IMVT (concentration in ppm) |
|---|---|---|---|---|---|---|---|---|---|
| 24 | 0.1 | 41.2 | 58.1 | 0.0 | 0.0 | 0.0 | 0.1 | 0.48 | 90 |
| 25 | 4.7 | 38.4 | 29.2 | 1.9 | 7.6 | 4.4 | 13.3 | 0.47 | 90 |
| 26 | 7.0 | 30.5 | 20.5 | 3.0 | 7.0 | 4.7 | 27.0 | 0.48 | 90 |
| 27 | 11.1 | 29.4 | 27.7 | 2.6 | 6.0 | 4.0 | 18.8 | 0.43 | 90 |
| 28 | 32.3 | 28.0 | 13.8 | 4.3 | 4.3 | 4.0 | 12.9 | 0.43 | 90 |
| 29 | 44.7 | 12.9 | 23.0 | 0.0 | 4.2 | 3.9 | 10.9 | 0.42 | 90 |
| 30 | 59.7 | 9.6 | 14.3 | 0.0 | 4.8 | 4.5 | 6.7 | 0.48 | 90 |
| 31 | 75.8 | 0.0 | 0.0 | 9.5 | 9.5 | 4.7 | 0.1 | 0.47 | 90 |
| 32 | 6.6 | 35.5 | 30.8 | 4.7 | 4.7 | 4.7 | 12.3 | 0.47 | 90 |
| 33 | 4.5 | 9.0 | 58.8 | 4.5 | 0.0 | 13.6 | 9.1 | 0.45 | 90 |
| 34 | 6.1 | 18.2 | 18.2 | 1.2 | 1.2 | 48.6 | 6.1 | 0.30 | 90 |
| 35 | 7.7 | 23.1 | 23.1 | 1.5 | 1.5 | 34.6 | 7.7 | 0.48 | 90 |
| 36 | 15.9 | 15.9 | 23.9 | 4.0 | 4.0 | 19.9 | 15.9 | 0.40 | 90 |
| 37 | 5.0 | 10.0 | 29.9 | 5.0 | 5.0 | 14.9 | 29.9 | 0.50 | 90 |

Note:
The amounts presented in the table above are weight percentages in the formulation.
Tint level is in ppm.

TABLE 4

Further examples of monomer mix formulations.

| Example | Ma2D37 Methacrylamide Crosslinker | TRIS [tris(trimethylsiloxy)-silylpropyl methacrylate] | N-Vinyl Pyrolidone | N,N-Dimethylacrylamide | 2-Hydroxyethyl methacrylate | Hexanol | M1-EDS6-TMS | Darocur 1173 | IMVT (concentration in ppm) |
|---|---|---|---|---|---|---|---|---|---|
| 38 | 0.1 | 41.2 | 58.1 | 0.0 | 0.0 | 0.0 | 0.1 | 0.48 | 145 |
| 39 | 4.7 | 38.4 | 29.2 | 1.9 | 7.6 | 4.4 | 13.3 | 0.47 | 145 |
| 40 | 7.0 | 30.5 | 20.5 | 3.0 | 7.0 | 4.7 | 27.0 | 0.48 | 145 |
| 41 | 11.1 | 29.4 | 27.7 | 2.6 | 6.0 | 4.0 | 18.8 | 0.43 | 145 |
| 42 | 32.3 | 28.0 | 13.8 | 4.3 | 4.3 | 4.0 | 12.9 | 0.43 | 145 |
| 43 | 44.7 | 12.9 | 23.0 | 0.0 | 4.2 | 3.9 | 10.9 | 0.42 | 145 |
| 44 | 59.7 | 9.6 | 14.3 | 0.0 | 4.8 | 4.5 | 6.7 | 0.48 | 145 |
| 45 | 75.8 | 0.0 | 0.0 | 9.5 | 9.5 | 4.7 | 0.1 | 0.47 | 145 |
| 46 | 6.6 | 35.5 | 30.8 | 4.7 | 4.7 | 4.7 | 12.3 | 0.47 | 145 |
| 47 | 4.5 | 9.0 | 58.8 | 4.5 | 0.0 | 13.6 | 9.1 | 0.45 | 145 |
| 48 | 6.1 | 18.2 | 18.2 | 1.2 | 1.2 | 48.6 | 6.1 | 0.30 | 145 |
| 49 | 7.7 | 23.1 | 23.1 | 1.5 | 1.5 | 34.6 | 7.7 | 0.48 | 145 |
| 50 | 15.9 | 15.9 | 23.9 | 4.0 | 4.0 | 19.9 | 15.9 | 0.40 | 145 |
| 51 | 5.0 | 10.0 | 29.9 | 5.0 | 5.0 | 14.9 | 29.9 | 0.50 | 145 |

Note:
The amounts presented in the table above are weight percentages in the formulation.
Tint level is in ppm.

TABLE 5

Further examples of monomer mix formulations.

| Example | Ma2D37 Methacrylamide Crosslinker | TRIS [tris(trimethylsiloxy)-silylpropyl methacrylate] | N-Vinyl Pyrolidone | N,N-Dimethylacrylamide | 2-Hydroxyethyl methacrylate | Hexanol |
|---|---|---|---|---|---|---|
| 52 | 0.1 | 41.2 | 58.1 | 0.0 | 0.0 | 0.0 |
| 53 | 4.7 | 38.4 | 29.2 | 1.9 | 7.6 | 4.4 |

TABLE 5-continued

Further examples of monomer mix formulations.

| | | | | | | |
|---|---|---|---|---|---|---|
| 54 | 6.6 | 35.6 | 30.8 | 4.7 | 4.7 | 4.7 |
| 55 | 6.6 | 35.6 | 30.8 | 4.7 | 4.7 | 0.0 |
| 56 | 6.6 | 35.6 | 30.8 | 4.7 | 4.7 | 0.0 |
| 57 | 7.0 | 30.5 | 20.5 | 3.0 | 7.0 | 0.0 |
| 58 | 11.1 | 29.4 | 27.7 | 2.6 | 6.0 | 4.0 |
| 59 | 32.3 | 28.0 | 13.8 | 4.3 | 4.3 | 0.0 |
| 60 | 44.7 | 12.9 | 23.0 | 0.0 | 4.4 | 0.0 |
| 61 | 59.7 | 9.6 | 14.3 | 0.0 | 4.8 | 0.0 |
| 62 | 75.8 | 0.0 | 0.0 | 9.5 | 9.5 | 4.7 |
| 63 | 6.6 | 35.5 | 30.8 | 4.7 | 4.7 | 4.7 |
| 64 | 4.5 | 9.0 | 58.8 | 4.5 | 0.0 | 0.0 |
| 65 | 6.1 | 18.2 | 18.2 | 1.2 | 1.2 | 0.0 |
| 66 | 7.7 | 23.1 | 23.1 | 1.5 | 1.5 | 34.6 |
| 67 | 15.9 | 15.9 | 23.9 | 4.0 | 4.0 | 0.0 |
| 68 | 5.0 | 10.0 | 29.9 | 5.0 | 5.0 | 0.0 |
| 69 | 9.5 | 35.5 | 30.8 | 4.7 | 4.7 | 4.7 |

| Example | Nonanol | t-Amyl alcohol | M1-EDS6-TMS | M1-BIS-EDS3-TMS | Darocur 1173 | IMVT (concentration in ppm) |
|---|---|---|---|---|---|---|
| 52 | 5.1 | 0.0 | 0.1 | 0.0 | 0.1 | 200 |
| 53 | 4.4 | 0.0 | 13.3 | 0.0 | 0.47 | 200 |
| 54 | 0.0 | 0.0 | 12.3 | 0.0 | 0.47 | 200 |
| 55 | 4.7 | 0.0 | 12.3 | 0.0 | 0.47 | 200 |
| 56 | 0.0 | 4.7 | 12.3 | 0.0 | 0.47 | 200 |
| 57 | 4.7 | 0.0 | 27.0 | 0.0 | 0.48 | 200 |
| 58 | 0.0 | 0.0 | 18.8 | 0.0 | 0.43 | 200 |
| 59 | 0.0 | 4.0 | 12.9 | 0.0 | 0.43 | 200 |
| 60 | 3.9 | 0.0 | 10.9 | 0.0 | 0.2 | 200 |
| 61 | 0.0 | 4.5 | 6.7 | 0.0 | 0.48 | 200 |
| 62 | 0.0 | 0.0 | 0.1 | 0.0 | 0.47 | 200 |
| 63 | 0.0 | 0.0 | 12.3 | 0.0 | 0.47 | 200 |
| 64 | 13.6 | 0.0 | 9.1 | 0.0 | 0.45 | 200 |
| 65 | 0.0 | 48.6 | 6.1 | 0.0 | 0.30 | 200 |
| 66 | 0.0 | 0.0 | 7.7 | 0.0 | 0.48 | 200 |
| 67 | 19.9 | 0.0 | 15.9 | 0.0 | 0.40 | 200 |
| 68 | 0.0 | 14.9 | 29.9 | 0.0 | 0.50 | 200 |
| 69 | 4.7 | 0.0 | 0.0 | 9.5 | 0.47 | 60 |

Note:
The amounts presented in the table above are weight percentages in the formulation.
Tint level is in ppm.

Disclosed in certain preferred embodiments of the invention herein is:

1. A monomer having a structural formula (I):

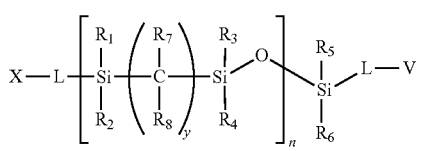

(I)

wherein X is the residue of a ring opening agent, L is the same or different and is a linker group or a bond and V is an ethylenically unsaturated polymerizable group, $R_1$, $R_2$, $R_3$, $R_4$, $R_5$, $R_6$ are independently H, alkyl, halo alkyl, cyclo alkyl, heterocyclo alkyl, alkenyl, halo alkenyl, or aromatic, $R_7$ and $R_8$ are independently H or alkyl wherein at least one of $R_7$ or $R_8$ is hydrogen, y is 2-7 and n is 1-100.

2. A monomer having a structural formula (II)

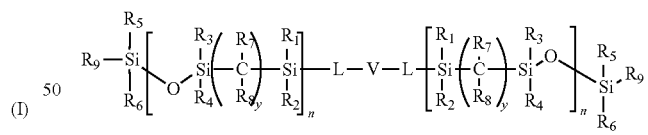

(II)

wherein L is the same or different and is a linker group or a bond and V is the same or different and is an ethylenically unsaturated polymerizable group, $R_1$, $R_2$, $R_3$, $R_4$, $R_5$, $R_6$ and $R_9$ are independently H, alkyl, halo alkyl, cyclo alkyl, heterocyclo alkyl, alkenyl, halo alkenyl, or aromatic, $R_7$ and $R_8$ are independently H or alkyl wherein at least one of $R_7$ or $R_8$ is hydrogen, y is 2-7 and n is 1-100.

3. A monomer according to claim 1 wherein the X is a residue of a ring opening agent selected from the group consisting of alkyl lithiums, alkoxides, trialkylsiloxylithiums and acrylic ester-capped polysiloxane prepolymers in the presence of an acid catalyst.

4. The monomer of claim 3 wherein the residue of the ring opening agent contains halo atoms.

5. The monomer of claim 1 wherein linker group is selected from the group consisting of substituted or unsubstituted alkyl, alkyl ether, alkenyls, alkenyl ethers, halo alkyls, substituted or unsubstituted siloxanes, and monomers capable of propagating ring opening.

6. The monomer of claim 2 wherein linker group is selected from the group consisting of substituted or unsubstituted alkyl, alkyl ether, alkenyls, alkenyl ethers, halo alkyls, substituted or unsubstituted siloxanes, and monomers capable of propagating ring opening.

7. The monomer of claim 1 having a structural formula (III):

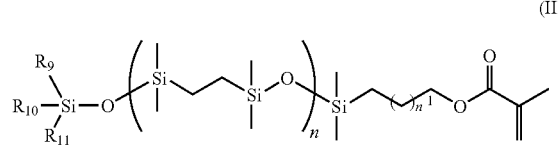

(III)

wherein $R_9$, $R_{10}$ and $R_{11}$ are independently H, alkyl, haloalkyl or other substituted alkyl groups, n is 1-100 and $n^1$ is 0-10.

8. The monomer of claim 1 having a structural formula (IV):

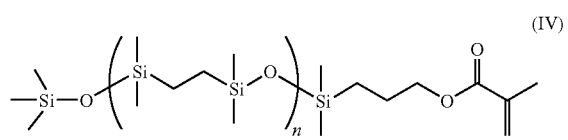

(IV)

wherein n is 1-100.

9. The monomer of claim 8 wherein n is 2-80.
10. The monomer of claim 8 wherein n is 3-20.
11. The monomer of claim 8 wherein n is 5-15.
12. A monomer of claim 1 wherein V is selected from the group consisting of acrylates, methacrylates, vinyl carbonates, O-vinyl carbamates, N-vinyl carbamates, acrylamides and methacrylamides.
13. A monomer of claim 2 wherein V is selected from the group consisting of acrylates, methacrylates, vinyl carbonates, O-vinyl carbamates, N-vinyl carbamates, acrylamides and methacrylamides.
14. The monomer of claim 1 having a structural formula selected from the group consisting of the following structural formulae:

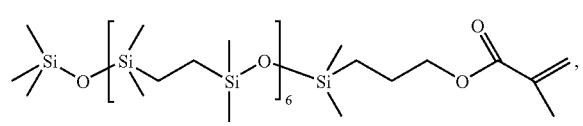

(V)

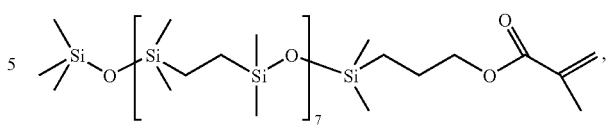

(VI)

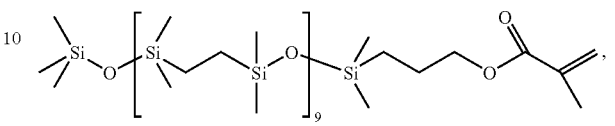

(VII)

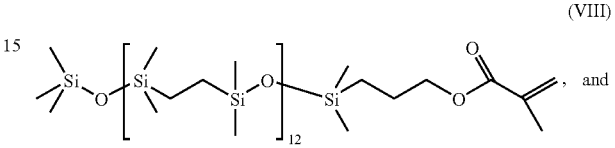

(VIII)

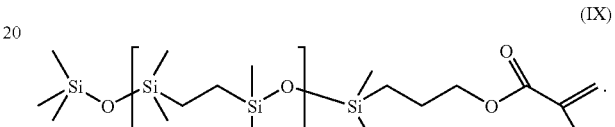

(IX)

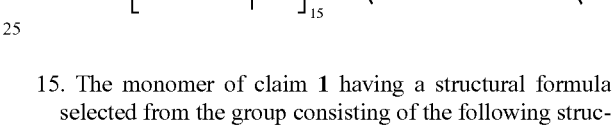

15. The monomer of claim 1 having a structural formula selected from the group consisting of the following structural formulae:

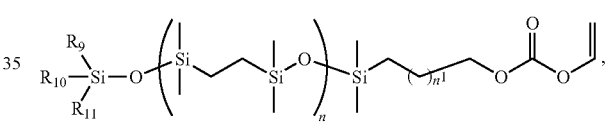

(X)

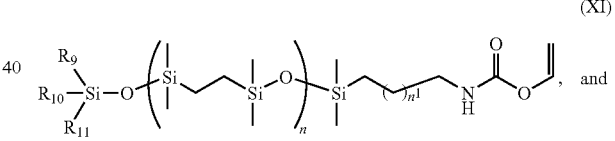

(XI)

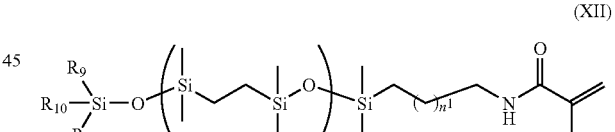

(XII)

wherein $R_9$, $R_{10}$ and $R_{11}$ are independently H, alkyl, haloalkyl or other substituted alkyl groups and n is 1-100 and $n^1$ is 0-10.

16. The monomer of claim 1 having a structural formula selected from the group consisting of the following structural formulae:

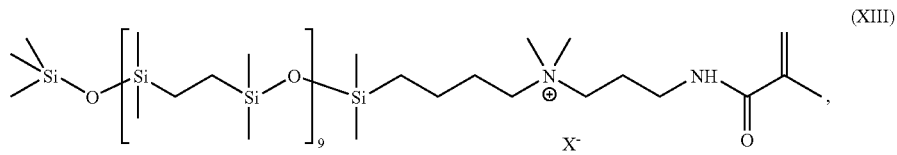

(XIII)

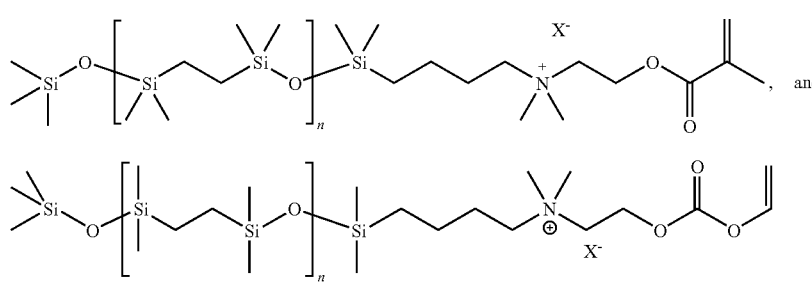

wherein n is 1-100 and X⁻ is a counterion to provide an overall neutral charge.

17. The monomer of claim 1 having the following structural formula:

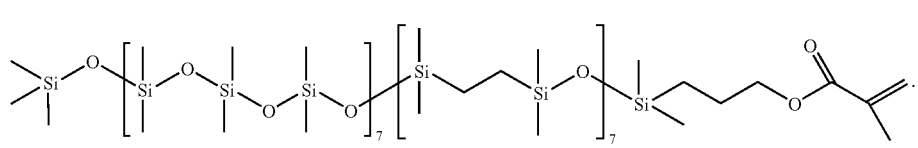

18. A monomer mix useful for forming a medical device wherein the monomer mix comprises at least one monomer selected from the group consisting of the monomers of claim 1 and when polymerized forms a medical device.

19. A monomer mix useful for forming a medical device wherein the monomer mix comprises at least one monomer selected from the group consisting of the monomers of claim 2 and when polymerized forms a medical device.

20. The monomer mix of claim 18 further comprising a second copolymerizable second monomer.

21. The monomer mix of claim 19 further comprising a second copolymerizable second monomer.

22. The monomer mix of claim 18 wherein the medical device formed is selected from the group consisting of rigid contact lenses, soft contact lenses, phakic intraocular lenses, aphakic intraocular lenses and corneal implants.

23. The monomer mix of claim 19 wherein the medical device formed is selected from the group consisting of rigid contact lenses, soft contact lenses, phakic intraocular lenses, aphakic intraocular lenses and corneal implants.

24. The monomer mix of claim 18 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.

25. The monomer mix of claim 19 wherein the medical device formed is selected from the group consisting of artificial heart valves, films, surgical devices, vessel substitutes, intrauterine devices, membranes, diaphragms, surgical implants, artificial blood vessels, artificial ureters, artificial breast tissue, membranes intended to come into contact with body fluid outside of the body, membranes for kidney dialysis machines, membranes for heart/lung machines, catheters, mouth guards, denture liners, ophthalmic devices, and hydrogel contact lenses.

26. The monomer mix of claim 24 wherein the medical device is a hydrogel contact lens.

27. The monomer mix of claim 25 wherein the medical device is a hydrogel contact lens.

28. The monomer mix of claim 18 wherein the at least one monomer selected from the group consisting of the monomers of claim 1 is an mono ethylenically unsaturated polycarbosiloxane monomer.

29. The monomer mix of claim 19 wherein the at least one monomer selected from the group consisting of the monomers of claim 2 is an mono ethylenically unsaturated polycarbosiloxane monomer.

30. The monomer mix of claim 28 wherein the mono ethylenically unsaturated polycarbosiloxane monomer is present in an amount from about 0.1 to about 30 percent by weight of the monomer mix.

31. The monomer mix of claim 28 wherein the mono ethylenically unsaturated polycarbosiloxane monomer is present in an amount from about 0.1 to about 20 percent by weight of the monomer mix.

32. The monomer mix of claim 28 wherein the mono ethylenically unsaturated polycarbosiloxane monomer is present in an amount from about 5 to about 15 percent by weight of the monomer mix.

33. The monomer mix of claim 29 wherein the mono ethylenically unsaturated polycarbosiloxane monomer is present in an amount from about 0.1 to about 30 percent by weight of the monomer mix.

34. The monomer mix of claim 29 wherein the mono ethylenically unsaturated polycarbosiloxane monomer is present in an amount from about 0.1 to about 20 percent by weight of the monomer mix.

35. The monomer mix of claim 29 wherein the mono ethylenically unsaturated polycarbosiloxane monomer is present in an amount from about 5 to about 15 percent by weight of the monomer mix.

36. The monomer mix of claim 20 wherein the second copolymerizable second monomer is a hydrophobic silicone containing monomer.

37. The monomer mix of claim 36 wherein the hydrophobic silicone containing monomer is present in the monomer mix between about 0.1 to about 75.8 percent by weight.

38. The monomer mix of claim 36 wherein the hydrophobic silicone containing monomer is present in the monomer mix between about 2 to about 20 percent by weight.

39. The monomer mix of claim 36 wherein the hydrophobic silicone containing monomer is present in the monomer mix between about 5 to about 13 percent by weight.

40. The monomer mix of claim 21 wherein the second copolymerizable second monomer is a hydrophobic silicone containing monomer.

41. The monomer mix of claim 40 wherein the hydrophobic silicone containing monomer is present in the monomer mix between about 0.1 to about 75.8 percent by weight.

42. The monomer mix of claim 40 wherein the hydrophobic silicone containing monomer is present in the monomer mix between about 2 to about 20 percent by weight.

43. The monomer mix of claim 40 wherein the hydrophobic silicone containing monomer is present in the monomer mix between about 5 to about 13 percent by weight.

44. The monomer mix of claim 20 wherein the second copolymerizable monomer is a non-silicone containing hydrophobic monomer.

45. The monomer mix of claim 21 wherein the second copolymerizable monomer is a non-silicone containing hydrophobic monomer.

46. The monomer mix of claim 20 wherein the non-silicone containing hydrophobic monomer is present at about 0 to about 60 percent by weight.

47. The monomer mix of claim 21 wherein the non-silicone containing hydrophobic monomer is present at about 0 to about 60 percent by weight.

48. The monomer mix of claim 20 wherein the non-silicone containing hydrophobic monomer is selected from the group consisting of alkyl acrylates and alkyl methacrylates.

49. The monomer mix of claim 21 wherein the non-silicone containing hydrophobic monomer is selected from the group consisting of alkyl acrylates and alkyl methacrylates.

50. The monomer mix of claim 20 wherein the second copolymerizable monomer is a bulky monomers selected from the group consisting of methacryloxypropyl tris(trimethylsiloxy)silane ("TRIS"), pentamethyldisiloxanyl methylmethacrylate, tris(trimethylsiloxy)methacryloxy propylsilane, phenyltretramethyl-disloxanylethyl acrylate, methyldi(trimethylsiloxy)methacryloxymethyl silane, 3-[tris(trimethylsiloxy)silyl]propyl vinyl carbamate, 3[tris (trimethylsiloxy)silyl]propyol allyl carbamate, and 3-[tris (trimethylsiloxy)silyl]propyl vinyl carbonate.

51. The monomer mix of claim 21 wherein the second copolymerizable monomer is a bulky monomers selected from the group consisting of methacryloxypropyl tris(trimethylsiloxy)silane ("TRIS"), pentamethyldisiloxanyl methylmethacrylate, tris(trimethylsiloxy)methacryloxy propylsilane, phenyltretramethyl-disloxanylethyl acrylate, methyldi(trimethylsiloxy)methacryloxymethyl silane, 3-[tris(trimethylsiloxy)silyl]propyl vinyl carbamate, 3[tris (trimethylsiloxy)silyl]propyol allyl carbamate, and 3-[tris (trimethylsiloxy)silyl]propyl vinyl carbonate.

52. The monomer mix of claim 50 wherein the bulky monomer is present at about 0 to about 41.2 percent by weight.

53. The monomer mix of claim 50 wherein the bulky monomer is present at about 34 to about 41 percent by weight.

54. The monomer mix of claim 50 wherein the bulky monomer is present at about 0 to about 25 to about 41 percent by weight.

55. The monomer mix of claim 51 wherein the bulky monomer is present at about 0 to about 41.2 percent by weight.

56. The monomer mix of claim 51 wherein the bulky monomer is present at about 34 to about 41 percent by weight.

57. The monomer mix of claim 51 wherein the bulky monomer is present at about 0 to about 25 to about 41 percent by weight.

58. The monomer mix of claim 26 wherein the monomer mix comprises a mixture containing at least one silicone-containing monomer and at least one hydrophilic monomer.

59. The monomer mix of claim 26 wherein the monomer mix comprises a separate crosslinker.

60. The monomer mix of claim 59 wherein the separate crosslinker is selected from the group consisting of methacrylates, ethylene glycol dimethacrylate (EGDMA) and allyl methacrylate (AMA).

61. The monomer mix of claim 60 wherein the separate crosslinker is present at between about 0 to about 76 percent by weight.

62. The monomer mix of claim 60 wherein the separate crosslinker is present at between about 2 to about 20 percent by weight.

63. The monomer mix of claim 60 wherein the separate crosslinker is present at between about 5 to about 13 percent by weight.

64. The monomer mix of claim 27 wherein the silicone-containing monomer is a crosslinking agent.

65. The monomer mix of claim 20 wherein the second copolymerizable monomer is a hydrophilic monomer.

66. The monomer mix of claim 65 wherein the hydrophilic monomer is selected from the group consisting of unsaturated carboxylic acids, methacrylic acids, acrylic acids; acrylic substituted alcohols, 2-hydroxyethyl methacrylate, 2-hydroxyethyl acrylate; vinyl lactams, N-vinylpyrrolidone (NVP), 1-vinylazonan-2-one; acrylamides, methacrylamide, N,N-dimethylacrylamide (DMA) and mixtures thereof.

67. The monomer mix of claim 65 wherein the hydrophilic monomer is present, separately or by combined weight in amounts of between about 0 to about 60 percent by weight.

68. The monomer mix of claim 65 wherein the hydrophilic monomer is present, separately or by combined weight in amounts between about 20 to about 45 percent by weight.

69. The monomer mix of claim 65 wherein the hydrophilic monomer is present, separately or by combined weight in amounts between about 0 to about 48.6 percent by weight.

70. The monomer mix of claim 65 wherein the hydrophilic monomer is present, separately or by combined weight in amounts between about 0 to about 30 percent by weight.

71. The monomer mix of claim 65 wherein the hydrophilic monomer is present, separately or by combined weight in amounts between about 0 to about 25 percent by weight.

72. The monomer mix of claim 65 wherein the hydrophilic monomer is present, separately or by combined weight in amounts between about 0 to about 9.5 percent by weight.

73. The monomer mix of claim 65 wherein the hydrophilic monomer is present, separately or by combined weight in amounts between about 2 to about 7 percent by weight.

74. The monomer mix of claim 21 wherein the second copolymerizable monomer is a hydrophilic monomer.

75. The monomer mix of claim 74 wherein the hydrophilic monomer is selected from the group consisting of unsaturated carboxylic acids, methacrylic acids, acrylic acids; acrylic substituted alcohols, 2-hydroxyethyl methacrylate, 2-hydroxyethyl acrylate; vinyl lactams, N-vinylpyrrolidone (NVP), 1-vinylazonan-2-one; acrylamides, methacrylamide, N,N-dimethylacrylamide (DMA) and mixtures thereof.

76. The monomer mix of claim 74 wherein the hydrophilic monomer is present, separately or by combined weight in amounts of between about 0 to about 60 percent by weight.
77. The monomer mix of claim 74 wherein the hydrophilic monomer is present, separately or by combined weight in amounts between about 20 to about 45 percent by weight.
78. The monomer mix of claim 74 wherein the hydrophilic monomer is present, separately or by combined weight in amounts between about 0 to about 48.6 percent by weight.
79. The monomer mix of claim 74 wherein the hydrophilic monomer is present, separately or by combined weight in amounts between about 0 to about 30 percent by weight.
80. The monomer mix of claim 74 wherein the hydrophilic monomer is present, separately or by combined weight in amounts between about 0 to about 25 percent by weight.
81. The monomer mix of claim 74 wherein the hydrophilic monomer is present, separately or by combined weight in amounts between about 0 to about 9.5 percent by weight.
82. The monomer mix of claim 74 wherein the hydrophilic monomer is present, separately or by combined weight in amounts between about 2 to about 7 percent by weight.
83. The monomer mix of claim 36 further comprising an organic diluent.
84. The monomer mix of claim 83 wherein the organic diluent is selected from the group consisting of alcohols, tert-butanol (TBA), tert-amyl alcohol, hexanol and nonanol; diols, ethylene glycol; polyols, glycerol and mixtures thereof.
85. The monomer mix of claim 83 wherein the organic diluent is present at about 0 to about 60% by weight of the monomeric mixture.
86. The monomer mix of claim 83 wherein the organic diluent is present at about 1 to about 40% by weight.
87. The monomer mix of claim 83 wherein the organic diluent is present at about 2 to about 30% by weight.
88. The monomer mix of claim 83 wherein the organic diluent is present at about 3 to about 25% by weight.
89. The monomer mix of claim 40 further comprising an organic diluent.
90. The monomer mix of claim 89 wherein the organic diluent is selected from the group consisting of alcohols, tert-butanol (TBA), tert-amyl alcohol, hexanol and nonanol; diols, ethylene glycol; polyols, glycerol and mixtures thereof.
91. The monomer mix of claim 89 wherein the organic diluent is present at about 0 to about 60% by weight of the monomeric mixture.
92. The monomer mix of claim 89 wherein the organic diluent is present at about 1 to about 40% by weight.
93. The monomer mix of claim 89 wherein the organic diluent is present at about 2 to about 30% by weight.
94. The monomer mix of claim 89 wherein the organic diluent is present at about 3 to about 25% by weight.
95. A hydrogel contact lens comprising a polymerized monomer mix comprising a polymerizable monomer mixture comprising about 0.1 to about 75.8 percent by weight of a methacrylamide crosslinker, about 0 to about 41.2 percent by weight of a bulky siloxane monomer, about 0 to about 78 percent by weight of at least one hydrophilic monomer, about 0 to about 48.6 percent by weight of an alcohol, about 0.1 to about 29.9 weight percent of an mono ethylenically unsaturated polycarbosiloxane monomer, about 0.1 to about 1.0 percent by weight of an initiator and about 90 to about 200 parts per million of a visibility tint.
96. The hydrogel contact lens of claim 95 comprising as part of polymerizable monomer mixture comprising about 5 to about 13 percent by weight of a methacrylamide crosslinker, about 34 to about 41 percent by weight of a bulky siloxane monomer, about 28 to about 52 percent by weight of at least one hydrophilic monomer, about 0 to about 25 percent by weight of an alcohol, about 5 to about 15 weight percent of an mono ethylenically unsaturated polycarbosiloxane monomer, about 0.2 to about 0.8 percent by weight of an initiator and about 90 to about 145 parts per million of a visibility tint.
97. The hydrogel contact lens of claim 95 comprising as part of polymerizable monomer mixture comprising about 2 to about 8 percent by weight of a methacrylamide crosslinker, about 25 to about 38 percent by weight of a bulky siloxane monomer, about 35 to about 45 percent by weight of at least one hydrophilic monomer, about 3 to about 8 percent by weight of an alcohol, about 10 to about 13 weight percent of an mono ethylenically unsaturated polycarbosiloxane monomer, about 0.3 to about 0.6 percent by weight of an initiator and about 145 to about 200 parts per million of a visibility tint.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:
1. A monomer having a structural formula (IV):

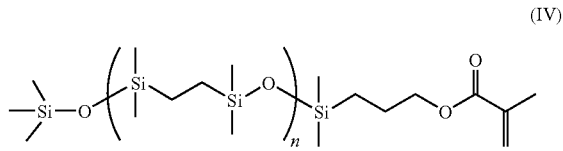

(IV)

wherein n is 2-80.
2. The monomer of claim 1 wherein n is 3-20.
3. The monomer of claim 1 wherein n is 5-15.
4. The monomer of claim 1 wherein the structural formula is selected from the group consisting of the following structural formulae:

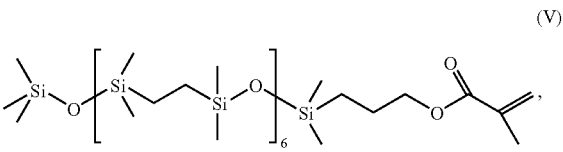

(V)

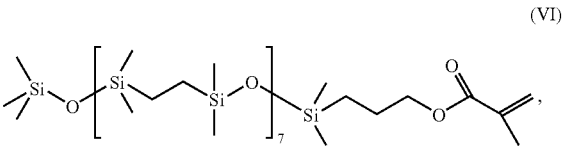

(VI)

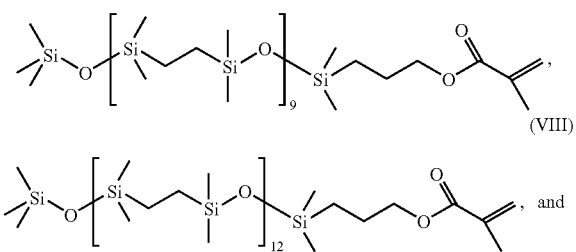
(VII)
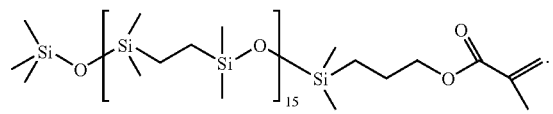
(IX)
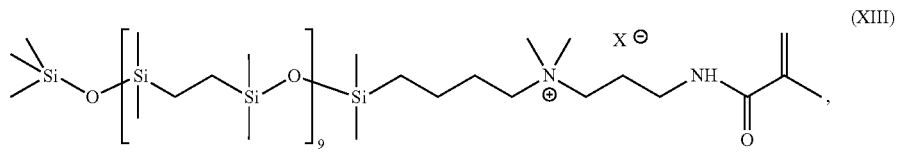
(VIII)
5. A monomer having a structural formula selected from the group consisting of the following structural formulae:
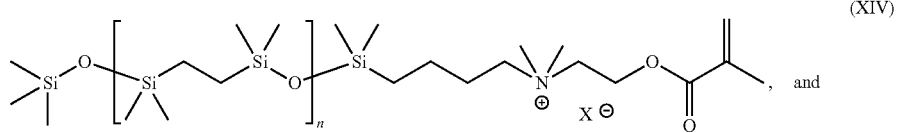
(XIII)
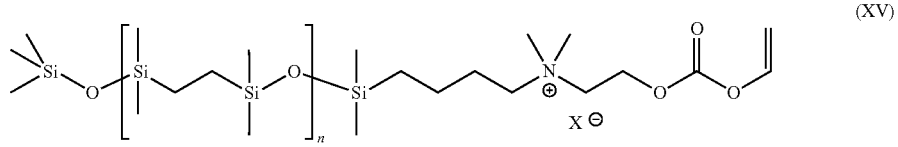
(XIV)
(XV)
wherein n is 1-100 and $X^-$ is a counterion to provide an overall neutral charge.
6. A monomer having the following structural formula:
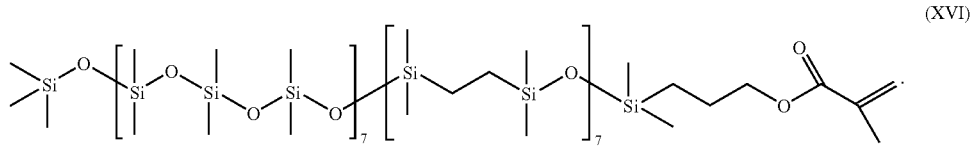
(XVI)
* * * * *